US010434266B2

United States Patent
Sasai et al.

(10) Patent No.: US 10,434,266 B2
(45) Date of Patent: Oct. 8, 2019

(54) NEBULIZER AND NEBULIZER KIT

(71) Applicant: OMRON HEALTHCARE CO., LTD., Muko-shi, Kyoto (JP)

(72) Inventors: Yoichi Sasai, Kyoto (JP); Shinichi Ito, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 596 days.

(21) Appl. No.: 15/240,018

(22) Filed: Aug. 18, 2016

(65) Prior Publication Data

US 2016/0354560 A1    Dec. 8, 2016

Related U.S. Application Data

(63) Continuation of application No. PCT/JP2015/053912, filed on Feb. 13, 2015.

(30) Foreign Application Priority Data

Feb. 27, 2014  (JP) ................................. 2014-037225

(51) Int. Cl.
*A61M 11/02* (2006.01)
*A61M 11/06* (2006.01)
(Continued)

(52) U.S. Cl.
CPC ........... *A61M 11/02* (2013.01); *A61M 11/002* (2014.02); *A61M 11/06* (2013.01);
(Continued)

(58) Field of Classification Search
CPC .............. A61M 11/001; A61M 11/002; A61M 11/007; A61M 11/02; A61M 11/06;
(Continued)

(56) References Cited

U.S. PATENT DOCUMENTS 1,839,193 A * 1/1932 Blanchard .............. A61M 11/06
128/200.18
3,097,645 A * 7/1963 Lester .................... A61M 11/06
128/200.21
(Continued)

FOREIGN PATENT DOCUMENTS

JP   05-184848 A   7/1993
JP   2000-504603 A   4/2000
(Continued)

OTHER PUBLICATIONS

Official Communication issued in International Patent Application No. PCT/JP2015/053912, dated Apr. 21, 2015.

*Primary Examiner* — Annette Dixon
(74) *Attorney, Agent, or Firm* — Keating and Bennett, LLP

(57) ABSTRACT

A nebulizer kit includes an atomizer generating an aerosol, and a particle sorting route communicating with the atomizer and sorting liquid particles in the aerosol to adjust a particle diameter distribution thereof, and guiding the aerosol to a discharge port. The particle sorting route includes a first particle sorting route with a uniform cross-sectional area in the first direction and a second particle sorting route with an inner end wall that curves from the first direction toward a second direction included in the same plane as the first direction. The first particle sorting route guides the aerosol to the second particle sorting route in the first direction, and the inner end wall of the second particle sorting route guides the aerosol in the second direction while aerosol particles with a certain particle diameter or more are attached thereto.

6 Claims, 19 Drawing Sheets

(51) Int. Cl.
  *A61M 11/00* (2006.01)
  *A61M 15/00* (2006.01)
  *A61M 15/08* (2006.01)
(52) U.S. Cl.
  CPC ........ *A61M 15/0021* (2014.02); *A61M 15/08* (2013.01); *A61M 2206/14* (2013.01)
(58) Field of Classification Search
  CPC .. A61M 15/00; A61M 16/0833; A61M 16/16; A61M 16/162; A61M 2202/064; A61M 2205/073; A61M 2209/08; A61M 2209/084; A63H 33/28; B05B 1/262; B05B 11/06; B05B 11/3001; B05B 7/0012; B05B 7/0483; B05B 7/2435; F23D 11/10; F24F 6/14; Y02B 30/545; Y10S 261/65
  See application file for complete search history.

(56) References Cited

U.S. PATENT DOCUMENTS

| | | | | |
|---|---|---|---|---|
| 3,744,722 A | * | 7/1973 | Burns | A61M 11/06 128/200.18 |
| 4,116,387 A | * | 9/1978 | Kremer, Jr. | A61M 11/06 239/338 |
| 4,251,033 A | * | 2/1981 | Rich | A61M 11/06 239/338 |
| 4,368,850 A | * | 1/1983 | Szekely | B05B 11/06 128/200.22 |
| 4,456,179 A | * | 6/1984 | Kremer | A61M 11/06 239/338 |
| 5,355,872 A | * | 10/1994 | Riggs | A61M 15/00 128/200.18 |
| 5,823,179 A | | 10/1998 | Grychowski et al. | |
| 6,527,151 B1 | | 3/2003 | Pavkov et al. | |
| 2010/0147292 A1 | | 6/2010 | Hamaguchi et al. | |
| 2014/0261401 A1 | | 9/2014 | Esaki et al. | |
| 2014/0263740 A1 | | 9/2014 | Esaki et al. | |

FOREIGN PATENT DOCUMENTS

| | | |
|---|---|---|
| JP | 2003-514660 A | 4/2003 |
| JP | 2007-097830 A | 4/2007 |
| JP | 2013-132471 A | 7/2013 |
| JP | 2013-132472 A | 7/2013 |
| WO | 2011/158715 A1 | 12/2011 |

\* cited by examiner (CONVENTIONAL TECHNOLOGY)

(CONVENTIONAL TECHNOLOGY)

(CONVENTIONAL TECHNOLOGY)

NEBULIZER AND NEBULIZER KIT

BACKGROUND OF THE INVENTION

1. Field of the Invention

The present invention relates to a nebulizer kit, and more specifically relates to a nebulizer kit that causes compressed gas to physically act on a liquid so as to generate and discharge an aerosol containing particles of the liquid.

Also, the present invention relates to a nebulizer provided with such a nebulizer kit, and a compressor that supplies compressed gas to the nebulizer kit.

2. Description of the Related Art

Nebulizers are used in inhalation treatments in which an atomized drug solution is allowed to directly act on the nasal cavity, upper respiratory tract, bronchial tubes, and the like. For example, a compressor-type nebulizer (jet-type nebulizer) disintegrates a drug solution using compressed air in order to atomize the drug solution, and generates and discharges an aerosol containing droplets (particles) of the drug solution.

Conventionally, as this type of nebulizer and nebulizer kit, there is a nebulizer composed of a nebulizer kit that generates an aerosol and a main body including a compressor for supplying compressed air to the nebulizer kit, as indicated in JP 2013-132472A, for example.

FIG. 17 is a perspective view of a conventional nebulizer body and a nebulizer kit disclosed in JP 2013-132472A. A nebulizer 2000 includes a main body 510, a compressed air pipe portion 512, a nebulizer kit 1000, and a mouthpiece 500. The main body 510 is equipped with a compressor that supplies compressed air to the nebulizer kit 1000 via the compressed air pipe portion 512 coupled to a compressed air vent 511, electronic components, and the like.

FIG. 18 is a cross-sectional view of the conventional nebulizer kit 1000. The nebulizer kit 1000 includes a particle sorter 1100, a flow path forming body 1150, a suction route forming body 1200, and a case body 1300.

The case body 1300 includes a compressed air introduction pipe 1313 through which compressed air G is introduced from the nebulizer body, and a liquid storage portion 1316 that stores the drug solution, and a nozzle hole 1315 is provided on an upper distal end portion 1313a of the compressed air introduction pipe 1313.

A suction route forming portion 1220 is provided on the suction route forming body 1200 in a state of being recessed from near the liquid storage portion 1316 to near the nozzle hole 1315, and near the nozzle hole 1315, the suction route forming portion 1220 and the outer wall of the compressed air introduction pipe 1313 of the case body 1300 form a liquid suction port 1240 from which the drug solution is discharged.

The flow path forming body 1150 is attached to the case body 1300 so as to cover the case body 1300, and includes an outer air introduction hole 1180 through which outer air A is introduced, an aerosol discharge port 1170, and an upper tube-shaped portion 1164.

The particle sorter 1100 includes a lower tube-shaped portion 1110 that guides an aerosol M1 upward, four blade portions 1140 that are provided above the lower tube-shaped portion 1110 and are curved and turn as the upper side is approached from below, and a central shaft portion 1130 that supports the four blade portions 1140.

With the conventional nebulizer kit 1000 having such a configuration, the compressed air ejected in the upward direction in the drawing from the nozzle hole 1315 causes negative pressure to occur near the liquid suction port 1240, whereby the drug solution stored in the liquid storage portion 1316 is sucked up into the suction route forming portion 1220 due to the effect of the negative pressure, and the drug solution is discharged from the liquid suction port 1240. The drug solution discharged from the liquid suction port 1240 is disintegrated by the compressed air ejected from the nozzle hole 1315, and after being disintegrated into fine particles, the drug solution is mixed with the compressed air to form an aerosol M1, which has an approximately upward momentum.

The aerosol M1 rises in the lower tube-shaped portion 1110 and advances to the region in which the blade portions 1140 are provided. Particles of the drug solution contained in the aerosol M1 that have large particle diameters attach to the blade portions 1140, and the blade portions 1140 change the flow of the aerosol into flows of aerosols M2a, M2c, and the like, which travel upward in the form of spirals.

The flows of the aerosols M2a, M2c, and the like, which travel upward in the form of spirals, are mixed in the upper tube-shaped portion 1164 to become an aerosol M3 having an approximately upward momentum, and are discharged from the aerosol discharge port 1170.

However, the conventional nebulizer kit has the following problems. Detailed description will be given with reference to FIG. 19.

FIG. 19 is an enlarged perspective view of the particle sorter 1100 of the conventional nebulizer kit 1000. Due to physical interaction with the four blade portions 1140 of the upper tube-shaped portion 1120 of the particle sorter 1100, the upward component of the momentum is reduced and a horizontal momentum is applied to the aerosol M1 having the approximately upward momentum as described above, thereby creating the flows of the aerosols M2a, M2b, M2c, and M2d, which rise in the form of spirals. In this case, the aerosol M1 first collides with the blade portions 1140 at an approximately perpendicular angle, and thereafter rises in a spiral shape while repeatedly colliding with the blade portions 1140, and therefore a considerable portion of the upward momentum energy needed to reach the aerosol discharge port 1170 (FIG. 18) is lost due to the mechanical interaction between the aerosol M1 and the blade portions 1140. In other words, the conventional nebulizer kit 1000 is configured to impede the flow of the aerosol in order to adjust the particle diameter of the drug solution contained in the aerosol, and for this reason, the efficiency of using compressed air has remained at a relatively low level.

SUMMARY OF THE INVENTION

In view of this, preferred embodiments of the present invention provide a nebulizer kit that improves efficiency of using compressed gas.

Also, preferred embodiments of the present invention provide a nebulizer including such a nebulizer kit and a compressor that supplies compressed gas to the nebulizer kit.

A nebulizer kit according to a preferred embodiment of the present invention includes an atomizer that generates an aerosol by atomizing a liquid; and a particle sorting route that is in communication with the atomizer, and sorts particles of the liquid included in the aerosol so as to adjust a particle diameter distribution of the particles of the aerosol, and thereafter guides the aerosol to a discharge port. The particle sorting route includes a first particle sorting route that extends in a first direction from the atomizer and has a uniform or substantially uniform cross-sectional area in the first direction, a second particle sorting route that is in communication with the first particle sorting route and includes an inner wall that curves from the first direction toward a second direction included in or substantially in the same plane as the first direction, and a third particle sorting route that is in communication with the second particle sorting route and extends in a direction parallel or substantially parallel to the first direction in a state of being shifted in a direction perpendicular or substantially perpendicular to the first direction. The first particle sorting route guides the aerosol ejected from the atomizer in a direction equal or substantially equal to the first direction to the second particle sorting route in the first direction. The inner end wall of the second particle sorting route guides the aerosol in the second direction, which is inclined with respect to the first direction, while particles with a particle diameter of a certain value or more among the particles of the aerosol are attached thereto. The third particle sorter has a cross-sectional area greater than an entire cross-sectional area of the second particle sorting route in the first direction, and allows the aerosol to flow to the discharge port, particles with a particle diameter of a certain value or more among the particles being attached to an inner wall thereof that is parallel or substantially parallel with the first direction and is inclined with respect to the second direction.

With this nebulizer kit, the aerosol generated by the atomizer reaches the second particle sorting route by being guided in a direction equal or substantially equal to the first direction by the first particle sorting route, which extends in the first direction from near the atomizer and has a uniform or substantially uniform cross-sectional area in the first direction. After reaching the second particle sorting route, the aerosol collides with the curved inner end wall of the second particle sorting route, and at that time, particles with a particle diameter of a certain value or more among the particles included in the aerosol are attached to the inner end wall, and the remaining particles are guided in a direction equal or substantially equal to the second direction, which is inclined with respect to the first direction. Then, the aerosol containing the rest of the particles reaches the third particle sorter (which extends in the direction parallel or substantially parallel to the first direction in a state of being shifted in the direction perpendicular to the first direction). Particles with a particle diameter of a certain value or more among the rest of the particles are attached to the inner wall, which is parallel or substantially parallel with the first direction and is inclined with respect to the second direction, and the third particle sorting route allows the rest of the aerosol to flow to the discharge port. Accordingly, particle sorting is performed using the inclined inner wall of the third particle sorter as well as the curved inner wall of the second particle sorter. As a result, it is possible to allow passage of particles with comparatively small particle diameters in comparison to the case of not using the third particle sorting route. Here, the inner end wall of the second particle sorting route curves from the first direction and is curved toward the second direction, which is included in or substantially in the same plane as the first direction. Accordingly, the aerosol is subjected to particle diameter sorting by collision with the inner end wall, but does not need to pass through a spiral sorting route as in the conventional technology at that time. Moreover, the third particle sorting route has a cross-sectional area greater than the entire cross-sectional area of the second particle sorting route in the first direction. Therefore, the flow of the aerosol is smoother than in the conventional technology, and the degree to which the particle sorting route inhibits the flow of aerosol is suppressed more in comparison to the conventional technology. For this reason, with the present nebulizer kit, the efficiency of using the compressed gas is improved relative to the conventional technology.

With a nebulizer kit according to a preferred embodiment of the present invention, the second particle sorting route and the third particle sorting route overlap with respect to the first direction, and in the third particle sorting route, outer air is allowed to flow toward the discharge port from a side near the atomizer with respect to a region at which the third particle sorting route overlaps with the second particle sorting route with respect to the first direction.

With the nebulizer kit of this preferred embodiment of the present invention, the aerosol that has entered the third particle sorting route from the second particle sorting route flows smoothly to the discharge port on the flow of outer air.

With a nebulizer kit according to a preferred embodiment of the present invention, the third particle sorting route extends in a direction parallel or substantially parallel to the first direction over a certain length or more from a terminal end of the inner end wall of the second particle sorting route on a side opposite to the first particle sorting route.

With the nebulizer kit of this preferred embodiment of the present invention, the flow of aerosol is adjusted so as to conform closely to the first direction at the portion of the third particle sorting route that extends over a certain length or more in the direction parallel or substantially parallel to the first direction from the terminal end of the inner end wall of the second particle sorting route on the side opposite to the first particle sorting route. For this reason, the aerosol in the adjusted flow moving in the first direction is able to be discharged from the discharge port. Accordingly, a case is prevented in which the aerosol ejecting performance changes due to the orientation of an opening portion of a mouth piece attached to the discharge port.

With a nebulizer kit according to a preferred embodiment of the present invention, the atomizer includes a compressed supply that ejects compressed gas in a direction parallel or substantially parallel to the first direction; and a liquid supplying member that is arranged on one side in an orientation of intersecting the first direction in a periphery of an opening portion of the compressed supply, and supplies a liquid to an ejection route for the compressed gas in accordance with negative pressure accompanying ejection of the compressed gas, and the compressed supply is such that on another side, which is opposite to the one side in the periphery of the opening portion, a wall surface of a compressed gas supply route is extended in or substantially in the first direction past an outer surface on the one side of the compressed supply.

With the nebulizer kit of this preferred embodiment of the present invention, the compressed supply is such that on another side, which is opposite to the one side in the periphery of the opening portion, a wall surface of the compressed gas supplying route is extended in or substantially in the first direction past the outer surface on the one side of the compressed supply. A majority of the compressed gas ejected from the compressed supply is directed in the direction from the compressed supply to the liquid supplying member by this extended portion. For this reason, the efficiency of generating the aerosol is improved.

With a nebulizer kit according to a preferred embodiment of the present invention, the atomizer ejects the aerosol such that in a speed distribution of a jet flow of the aerosol with respect to a direction perpendicular or substantially perpendicular to the first direction, more speed components in a direction opposite to the second direction are included than speed components in the second direction.

With the nebulizer kit of this preferred embodiment of the present invention, the aerosol generated by the atomizer is caused to collide efficiently with the inner end wall of the second particle sorting route. For this reason, particle sorting is performed efficiently by using the inner end wall.

A nebulizer kit according to a preferred embodiment of the present invention includes an atomizer that generates an aerosol by atomizing a liquid; and a particle sorting route that is in communication with the atomizer, and sorts particles of the liquid included in the aerosol so as to adjust a particle diameter distribution of the particles of the aerosol, and thereafter guides the aerosol to a discharge port. The atomizer may include a compressed supply that ejects compressed gas in a direction parallel or substantially parallel to the first direction; and a liquid supplying member that is arranged on one side in an orientation of intersecting the first direction in a periphery of an opening portion of the compressed supply, and supplies a liquid to an ejection route for the compressed gas in accordance with negative pressure accompanying ejection of the compressed gas. The compressed supply is such that on another side, which is opposite to the one side in the periphery of the opening portion, a wall surface of a compressed gas supply route is extended in or substantially in the first direction past an outer surface on the one side of the compressed supply.

With this nebulizer kit, the compressed supply of the atomizer is such that on the other side, which is opposite to the one side in the periphery of the opening portion, the wall surface of the compressed gas supply route is extended in or substantially in the first direction past the outer surface on the one side of the compressed supply. A majority of the compressed gas ejected from the compressed supply by this extended portion is directed in the direction from the compressed supply to the liquid supplying member. For this reason, the efficiency of generating the aerosol is improved.

A nebulizer according to a preferred embodiment of the present invention includes a main body including a compressor that discharges compressed gas; a compressed gas pipe portion through which the compressed gas discharged from the compressor is introduced; and a nebulizer kit according to one of the preferred embodiments of the present invention described above that generates the aerosol using the compressed air supplied through the compressed gas pipe portion.

In the present specification, "liquid particle" and "droplet" are used with almost the same meaning. Also, in the present specification, "aerosol" is a mixture of a gas and liquid particles.

As is evident from the description above, the efficiency of using compressed gas is improved with the nebulizer kit of various preferred embodiments of the present invention. Also, the nebulizer kit is able to be used as a nebulizer kit for a compressor-type nebulizer. With a nebulizer including the present nebulizer kit, it is possible to improve the efficiency of using compressed gas.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described in detail with reference to the drawings.

Figure 1:
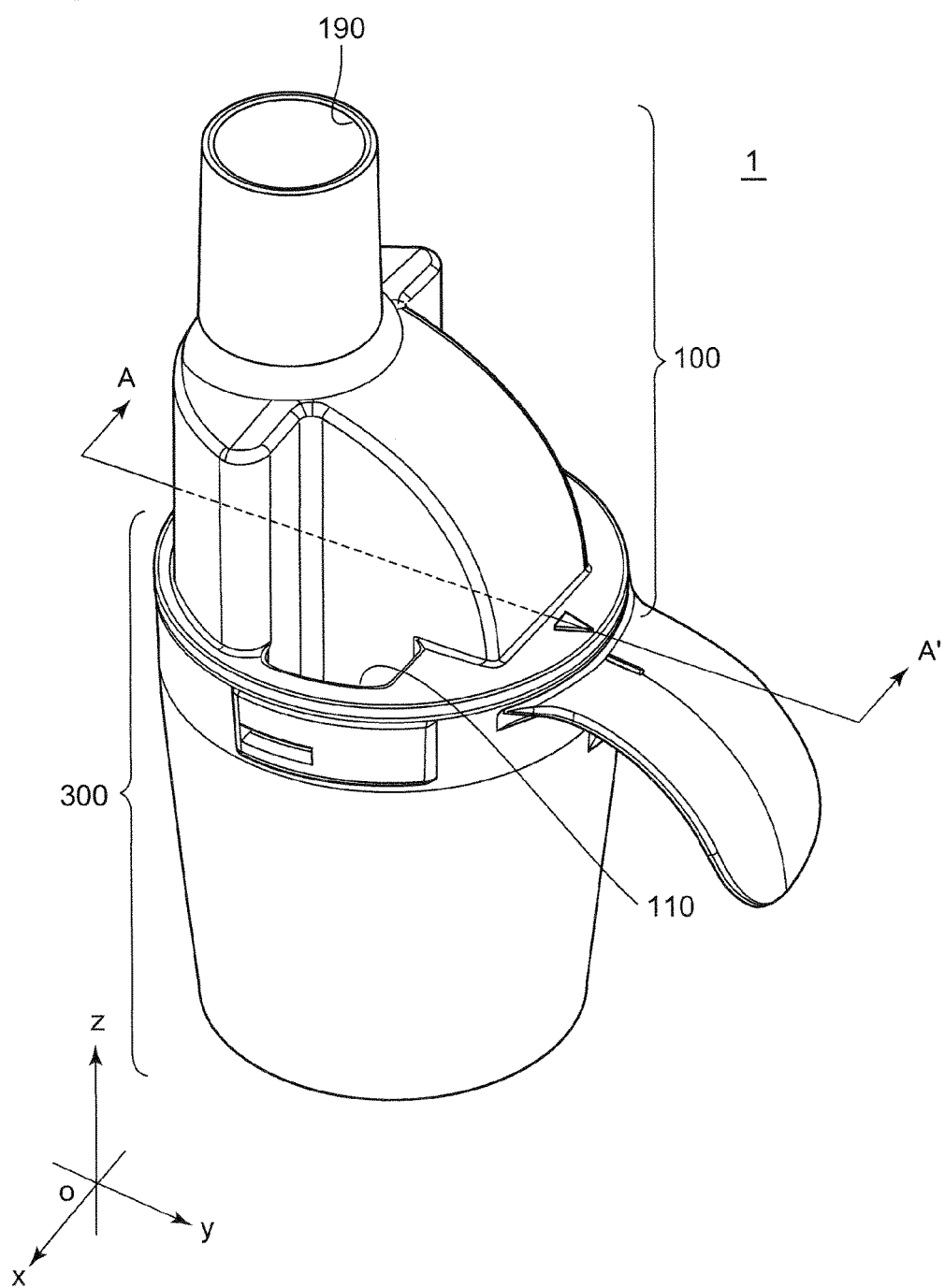
FIG. 1 is a perspective view showing a nebulizer kit according to a preferred embodiment of the present invention.
Figure 17:
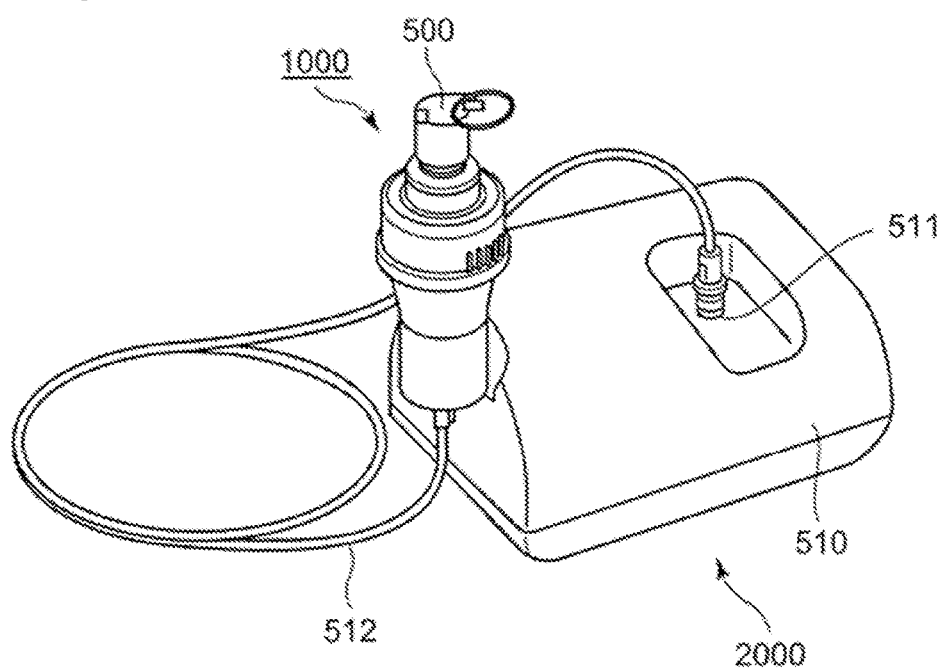
FIG. 17 is a perspective view showing a conventional nebulizer.
Figure 18:
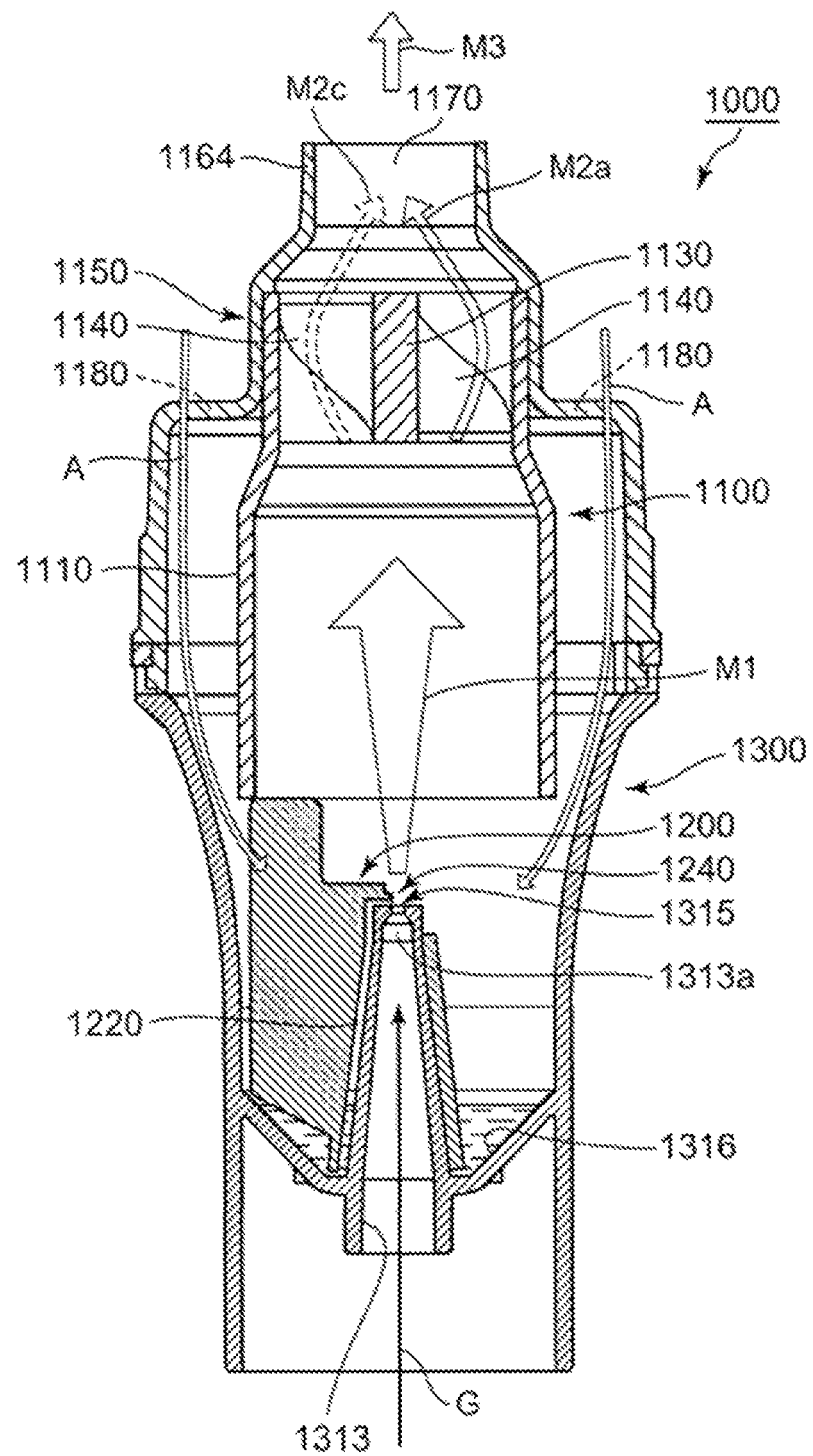
FIG. 18 is a cross-sectional view showing a conventional nebulizer kit.
Figure 19:
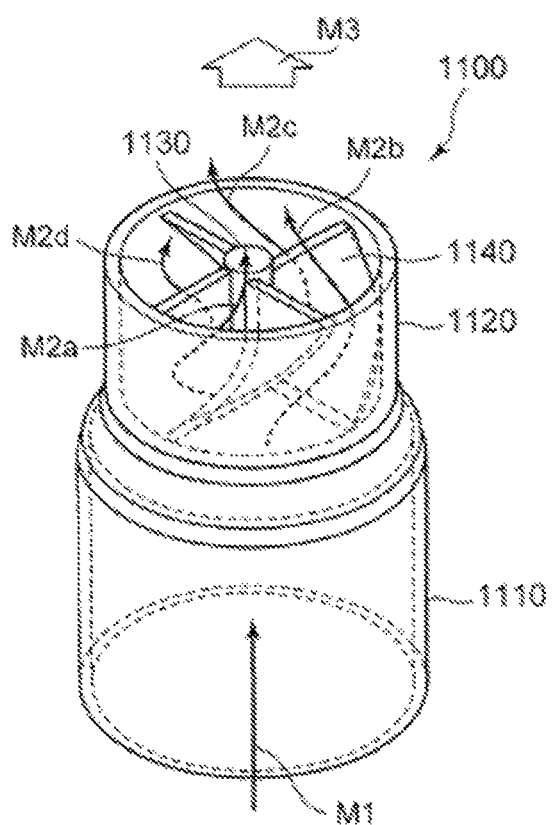
FIG. 19 is a perspective view showing a particle sorter of a conventional nebulizer kit.

FIG. 1 is a perspective view of a nebulizer kit 1 according to a preferred embodiment of the present invention. For example, polypropylene (PP) can be used as the material of the nebulizer kit 1, but there is no limitation to this. The nebulizer kit 1 includes a particle sorter 100 provided with an outer air introduction hole 110 and a (aerosol) discharge port 190, and a case body 300 into which the particle sorter 100 can be tightly fit. Also, the case body 300 contains a later-described suction route forming body 200. The nebulizer kit 1 can connect to a nebulizer main body (not shown) via a compressed gas pipe (tube), and can introduce compressed gas (such as air) supplied by a compressor in the nebulizer main body. Because the nebulizer main body and the compressed gas pipe may be a conventional nebulizer main body and a tube such as those illustrated in FIG. 17 or the like, description thereof will not be included here. Also, a mouthpiece, an inhalation mask, a nose piece, or the like can be mounted on the discharge port 190. The mouthpiece, inhalation mask, nose piece, and the like in this context may be conventionally-used items, and therefore description thereof will not be included here.

Figure 2:
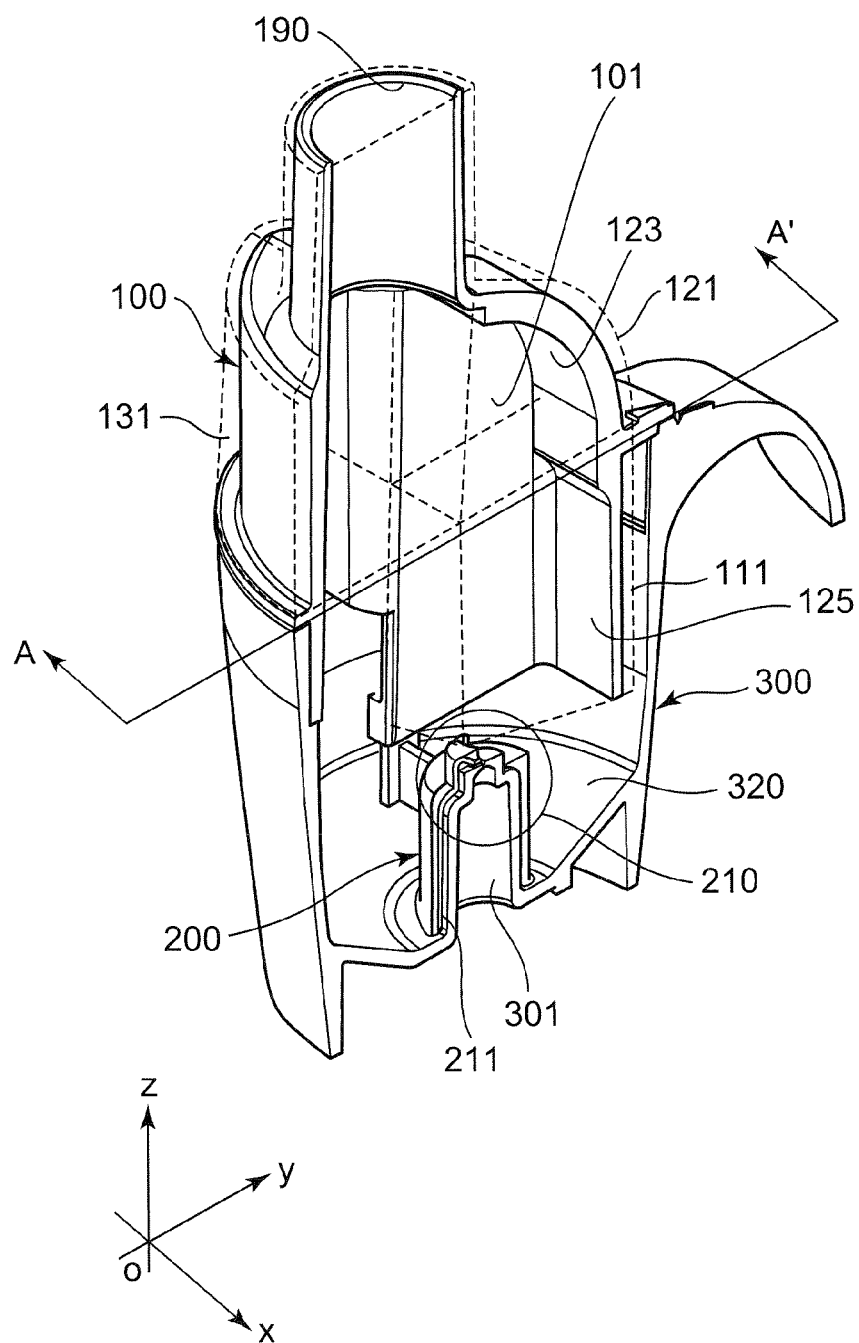
FIG. 2 is a cross-sectional perspective view of a nebulizer kit taken along line A-A' in FIG. 1.
Figure 3:
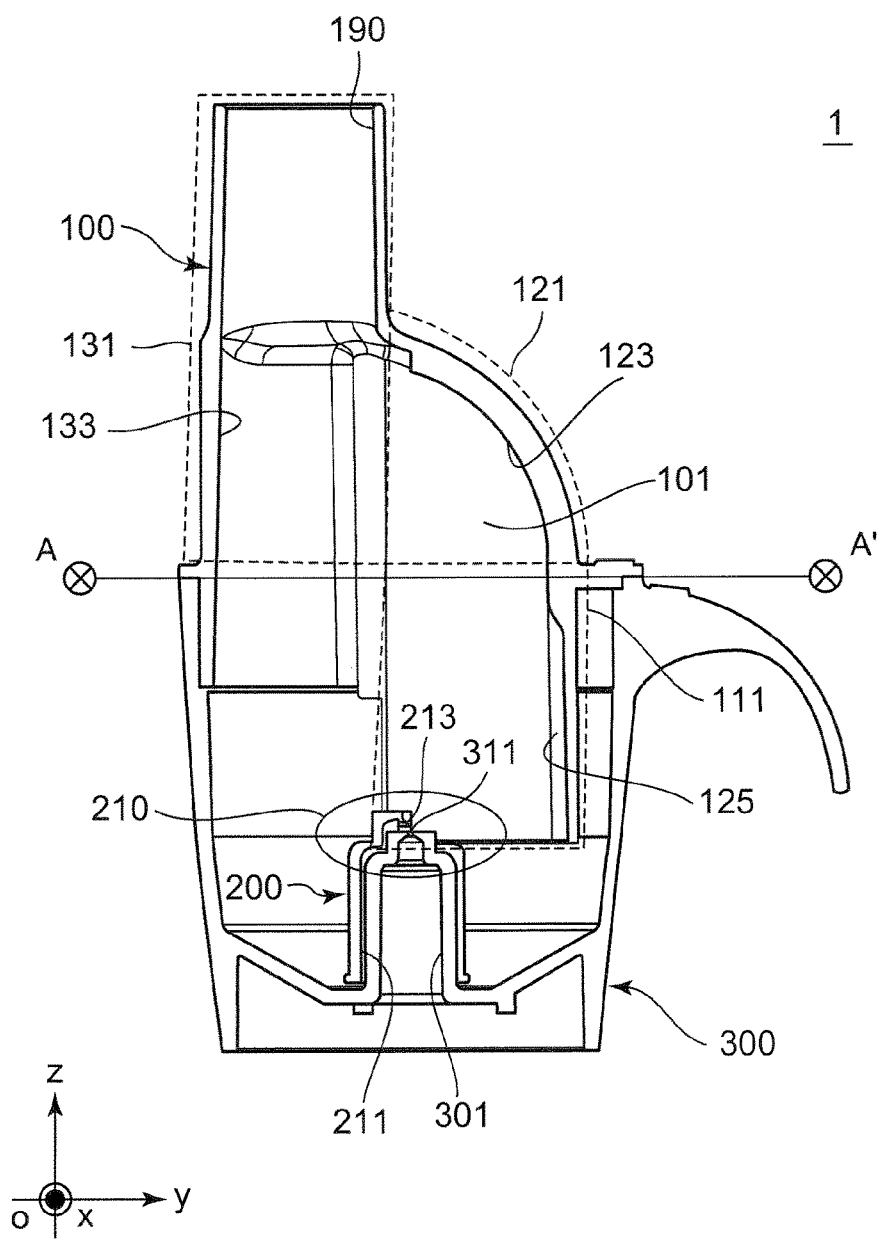
FIG. 3 is a cross-sectional view of a nebulizer kit taken along line A-A' in FIG. 1.

FIG. 2 is a cross-sectional perspective view showing a cross section taken along line A-A' in FIG. 1 of the nebulizer kit 1. Also, FIG. 3 is a cross-sectional view showing a cross section taken along line A-A' in FIG. 1 of the nebulizer kit 1. The configuration of the nebulizer kit 1 will be described with reference to FIGS. 2 and 3.

The case body 300 has a tube shape with an open upper portion and a closed lower portion, and the lower bottom portion thereof constitutes a liquid storage portion 320 that stores a liquid such as a drug solution. A compressed gas introduction pipe 301 for introducing a compressed gas (such as air) from the nebulizer main body (not shown) via the compressed gas pipe (tube) is formed at the center of the bottom portion. The upper distal end of the compressed gas introduction pipe 301 is closed, and a nozzle hole 311 is provided at a central portion on the upper end surface thereof. The nozzle hole 311 penetrates through the upper end surface of the compressed gas introduction pipe 301. The nozzle hole 311 and a later-described liquid suction port 213 of the suction route forming body 200 form an atomizer 210 that atomizes the liquid (such as water, physiological saline solution, or a vaccine) stored in the liquid storage portion 320 so as to generate an aerosol.

The suction route forming body 200 has an inner wall that coincides with the outer wall of the compressed gas introduction pipe 301, and a portion of the inner wall is provided with a groove (suction route forming portion 211). This groove (suction route forming portion 211) forms a pipe portion (suction route) with the outer wall of the compressed gas introduction pipe 301 when the suction route forming body 200 and the compressed gas introduction pipe 301 are fitted onto each other. The suction route forming body 200 has an opening at a portion on the upper end thereof so that the nozzle hole 311 of the compressed gas introduction pipe 301 of the case body 300 is exposed when the suction route forming body 200 is placed on the case body 300. Also, the upper end of the suction route forming body 200 is provided with a liquid suction port 213, which is one end of the suction route forming portion 211, near the nozzle hole 311. The liquid suction port 213 is an opening portion that can discharge a drug solution sucked up along the suction route.

The particle sorter 100 includes first, second, and third particle sorting routes 111, 121, and 131 that guide the aerosol generated by the atomizer 210 to the discharge port 190, and can be fit tightly on the case body 300 by being aligned in the circumferential direction. The first, second, and third particle sorting routes 111, 121, and 131 are in communication with the atomizer 210, and form a particle sorting route that sorts the particles of the liquid contained in the aerosol so as to adjust the distribution of the particle diameters of the aerosol particles and thereafter guide the aerosol to the discharge port. Also, the particle sorter 100 can be aligned so as to fit such that it is in a predetermined positional relationship with a later-described rectangular shape (FIGS. 6, 7, etc.) of the nozzle hole 311 of the compressed gas introduction pipe 301 of the case body 300 when fitted onto the case body 300. The predetermined positional relationship need only be a positional relationship in which the aerosol generated using the gas ejected from the nozzle hole 311 is efficiently guided to the first particle sorting route 111.

The first particle sorting route 111 is a region having an approximately rectangular shape in a cross section orthogonal to the z-axis direction (first direction), the region being surrounded on three sides by two partitions, namely an inner partition 101 parallel to the y-z plane and a corresponding inner partition (arranged parallel to the inner partition 101 in a region in which x is positive (not shown)), and a tube-shaped portion inner wall 125 of the particle sorter 100. As shown in the drawings, the first particle sorting route 111 is a region that has a substantially uniform rectangular cross section extending in the z direction (first direction) from near the atomizer 210. The first particle sorting route 111 can function as a route that upwardly guides the aerosol ejected substantially in the z-axis direction (first direction) at the atomizer 210, and because the cross-sectional area of the route is uniform in the z-axis direction, the first particle sorting route 111 can guide the aerosol upward rapidly without diminishing the initial momentum of the jet flow of the aerosol, and can guide the aerosol to the second particle sorting route 121 in communication with the upper end thereof.

The second particle sorting route 121 is a region surrounded on three sides by two partitions, namely the inner partition 101 and a corresponding inner partition (not shown), and an inner end wall 123 that gradually curves from a first direction (z-axis direction) along the y-z plane toward a direction (second direction) that is included in substantially the same plane (y-z plane) as the first direction, approximately coincides with the y-axis negative direction, and is inclined slightly in the +z direction. In the second particle sorting route 121, the aerosol that rises through the first particle sorting route 111 collides with the inner end wall 123. Due to this collision, particles with a particle diameter of a certain value or more among the particles in the liquid contained in the aerosol are attached with high reliability to the inner end wall 123, or are each further divided into multiple particles with smaller particle diameters due to collision with the inner end wall 123. On the other hand, particles with particle diameters less than the certain value are reflected in a second direction (direction that approximately coincides with the y-axis negative direction and is slightly inclined in the +z direction) with high reliability. Note that the second particle sorting route 121 is in communication with the third particle sorting route 131 on the side opposite to the side in communication with the first particle sorting route 111, and can guide the aerosol generated by the atomizer 210 toward the third particle sorting route 131.

The third particle sorting route 131 is a region that overlaps with the second particle sorting route 121 with respect to the first direction at a portion and is defined by the inner wall 133 on the side opposite thereto. The third particle sorting route 131 has an approximately semi-ellipsoid shape in a cross section orthogonal to the z-axis direction (first direction). The cross-sectional area in the z-axis direction (first direction) of the third particle sorting route is larger than the cross-sectional area in the z-axis direction (first direction) of the second particle sorting route 121. Also, the inner wall 133 that defines the third particle sorting route 131 extends in the z-axis direction (first direction), and accordingly, the inner wall 133 is inclined with respect to the second direction (direction that approximately coincides with the y-axis negative direction and is slightly inclined in the +z direction). For this reason, a portion of the aerosol that advances in the second direction to the third particle sorting route 131 from the second particle sorting route 121 reaches the inner wall 133 while the speed of the aerosol is reduced due to the enlargement of the size of the flow path. In a similar manner to the particle sorting resulting from the physical interaction with the inner end wall 123 on the second particle sorting route 121, particles with a particle diameter of a certain value or more among the particles in the liquid in the aerosol that reaches the inner wall 133 are attached to the inner wall 133 or are each further divided into multiple particles with smaller particle diameters due to the collision with the inner wall 133 with high reliability. On the other hand, particles with a particle diameter smaller than the certain value are reflected with high reliability in a direction that approximately coincides with the y-axis positive direction and is slightly inclined in the +z direction. The aerosol subjected to particle sorting in this manner is transported to the discharge port 190 on a flow of outside air traveling upward from the lower portion of the third particle sorting route 131 and is discharged. Also, the third particle sorting route 131 furthermore extends a certain length in the first direction (z-axis direction) from the upper end of the inner end wall 123 of the second particle sorting route 121. With this configuration, the flow of the aerosol flows uniformly in the first direction (z axis direction), and has at least relatively little turbulence, whereby change in the amount of aerosol discharged according to the orientation of the opening of a mouthpiece or the like (not shown) mounted on the discharge port 190 is at least suppressed.

With the nebulizer kit 1, the aerosol generated by the atomizer 210 is guided in a direction that is substantially equal to the first direction (z-axis direction) from the atomizer 210 by the first particle sorting route 111, and reaches the second particle sorting route 121. On the second particle sorting route 121, particle sorting of the aerosol is performed due to the physical interaction with the inner end wall 123, and the aerosol subjected to particle sorting flows in the second direction. Here, the inner end wall 123 is curved so as to curve from the first direction (z-axis direction) toward the second direction (a direction that approximately coincides with the y-axis negative direction and is slightly inclined in the +z direction) included substantially in the same plane (y-z plane) as the first direction. The aerosol does not pass through a spiral sorting route as in the conventional technology, and thus the flow of the aerosol is smoother than in the conventional technology and the degree to which the particle sorting route inhibits the flow of the aerosol can be suppressed more than in the conventional technology. For this reason, with the present nebulizer kit, the efficiency of using the compressed gas is improved relative to the conventional technology.

Figure 4A:
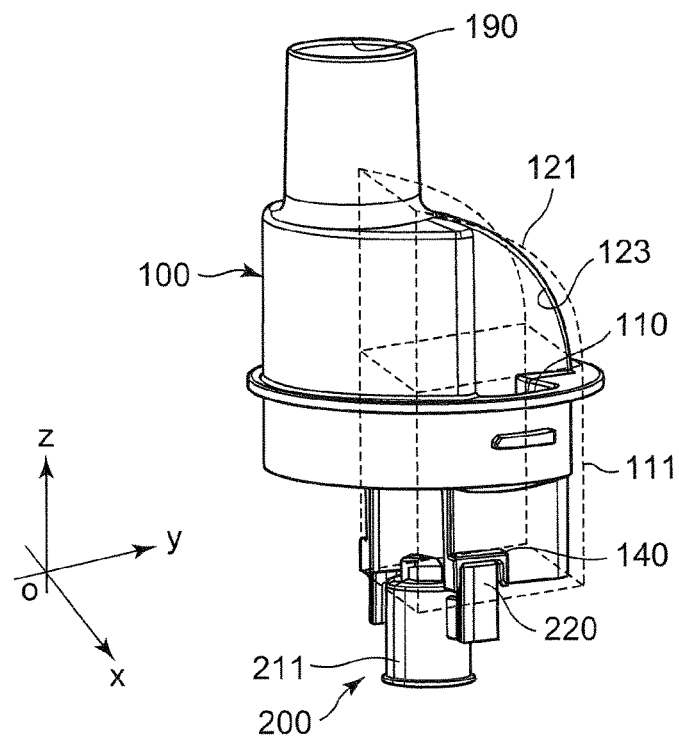
FIG. 4A is a perspective view showing engagement between a particle sorter and a suction route forming body.
Figure 4B:
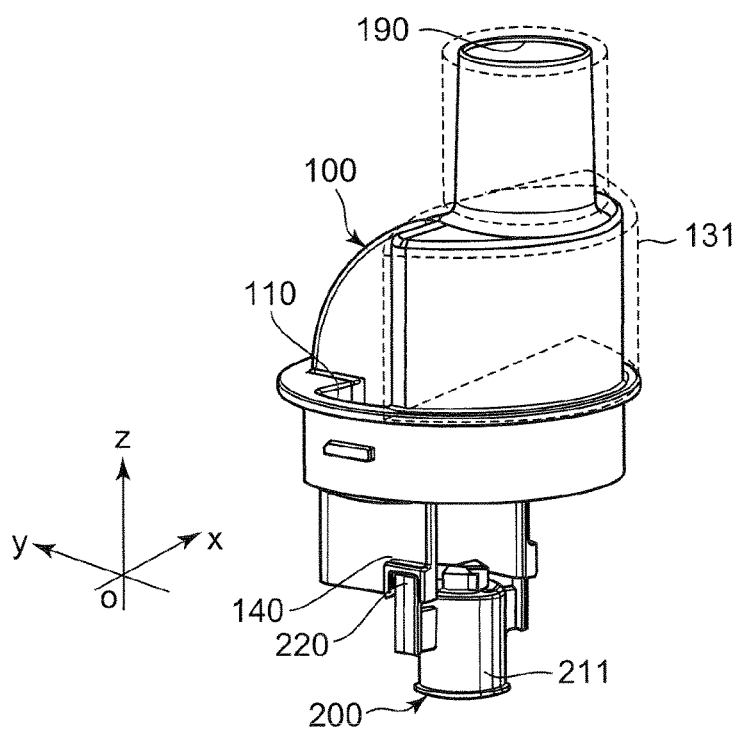
FIG. 4B is a perspective view showing engagement between a particle sorter and a suction route forming body.
Figure 5:
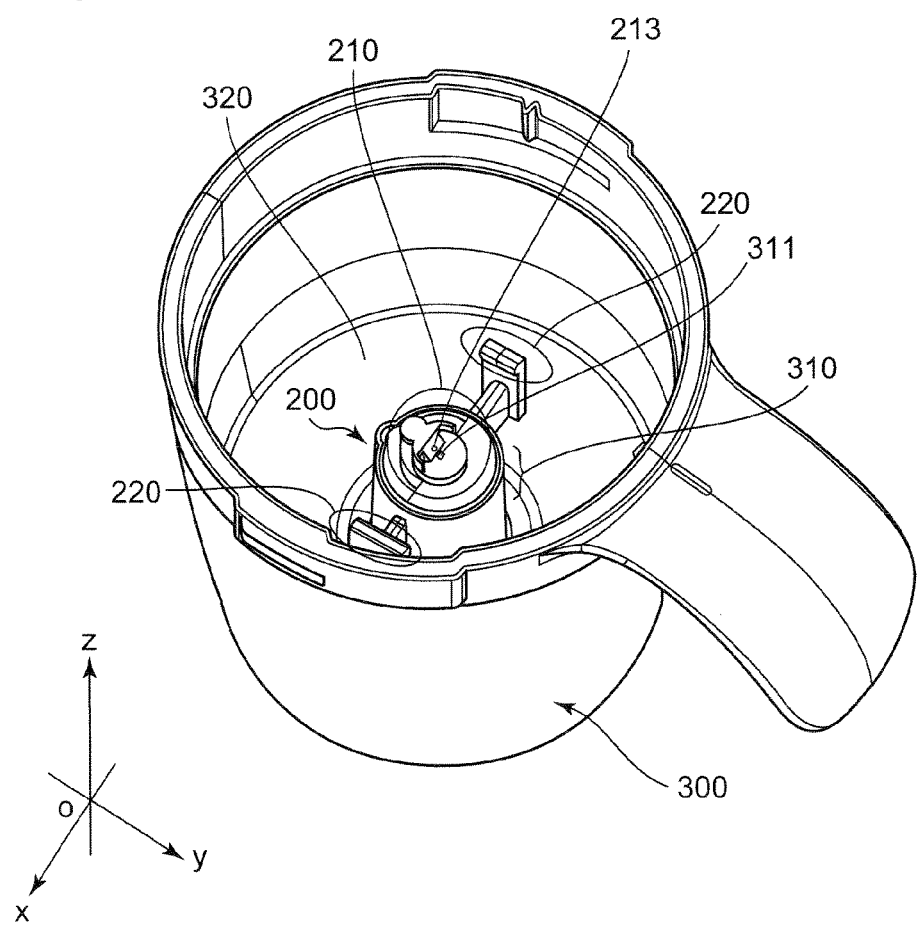
FIG. 5 is a perspective view showing an atomizer formed by the suction route forming body and a case body.

FIGS. 4A and 4B are perspective views for showing a mode of engagement between the particle sorter 100 and the suction route forming body 200. Note that display of the case body 300 is omitted in both drawings. The suction route forming body 200 has two fixing claw portions 220, and the particle sorter 100 has claw receiving portions 140 for receiving the fixing claw portions 220 of the suction route forming body 200. Due to the claw receiving portions 140 receiving the fixing claw portions 220, the relative positions of the particle sorter 100 and the suction route forming body 200 can be fixed with respect to the circumferential direction of the nebulizer kit 1. In other words, fixing the suction route forming body 200 to the particle sorter 100 suppresses the occurrence of a difference in performance between the two caused by an error in the dimensions of the portions, and furthermore, due to the fixing claw portions 220 being received by the claw receiving portions 140, the positional relationship in the circumferential direction between the atomizer 210 and the first, second, and third particle sorting routes 111, 121, and 131 is fixed. At this time, as shown in FIG. 5, the atomizer 210 is fixed in position such that the liquid suction port 213 is located on a side opposite to the first particle sorting route 111 with respect to the nozzle hole 311.

Figure 6:
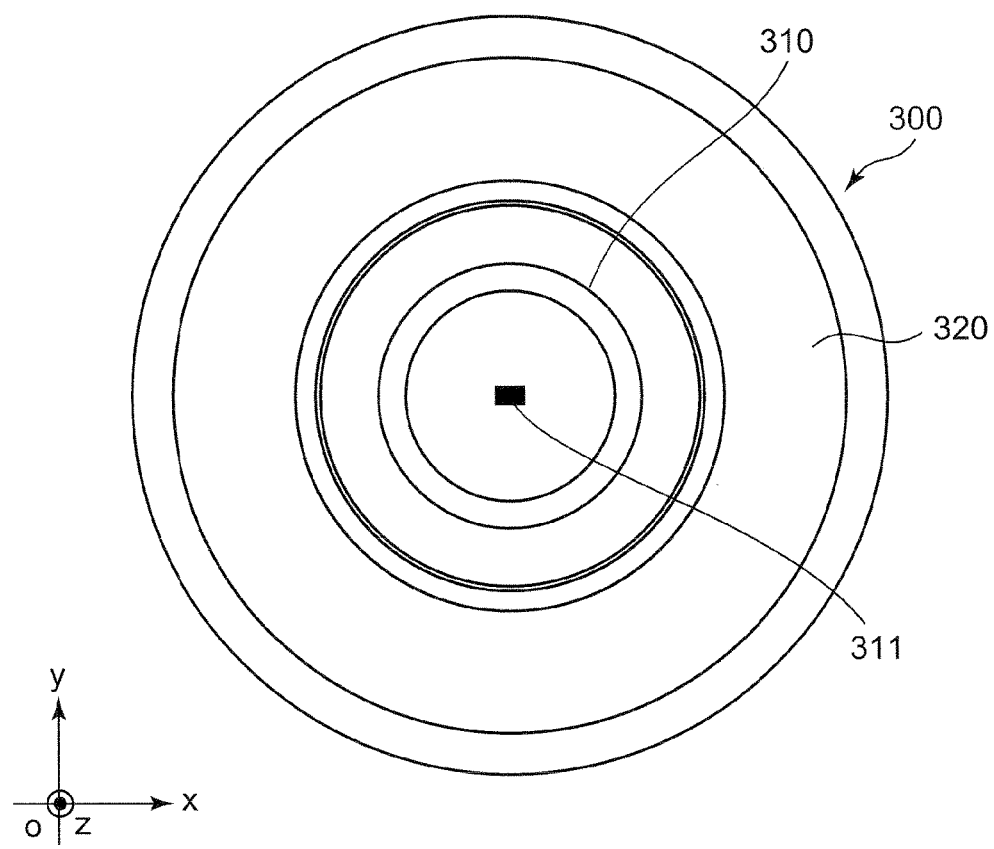
FIG. 6 is a plan view of the case body.
Figure 7:
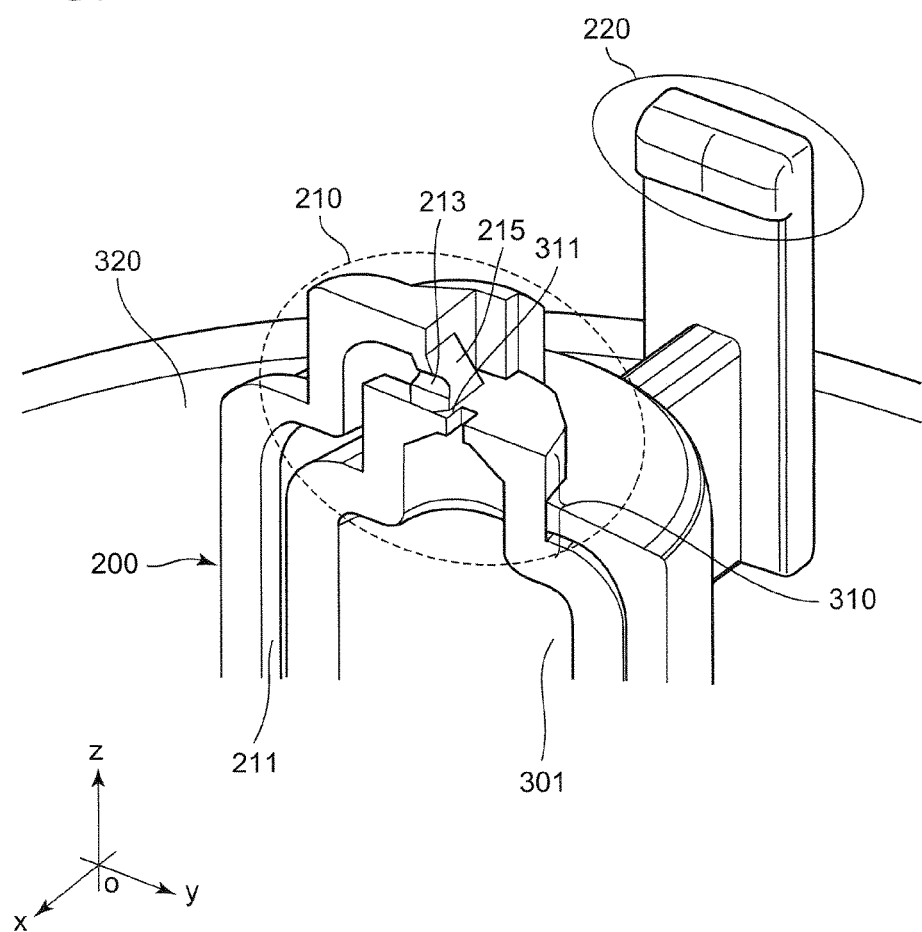
FIG. 7 is an enlarged cross-sectional perspective view showing a configuration of the atomizer.
Figure 8:
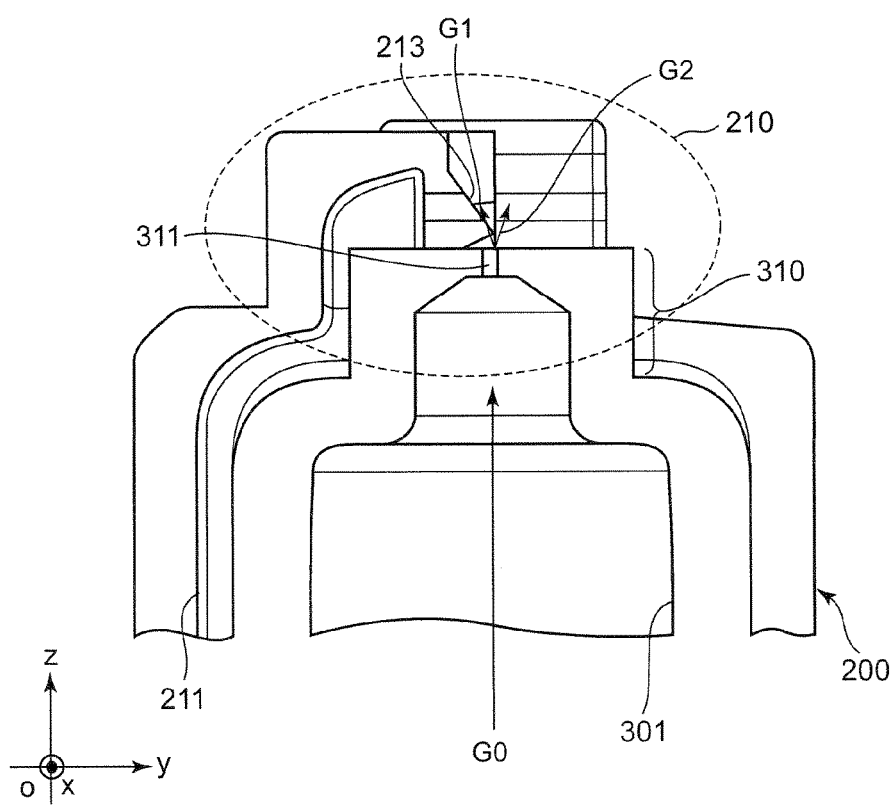
FIG. 8 is an enlarged cross-sectional view showing a configuration of the atomizer.

Next, details of the configuration of the atomizer 210 will be described with reference to FIGS. 6, 7, and 8. FIG. 6 is a plan view of the case body 300, showing a configuration of the case body 300 near the nozzle hole 311. FIG. 7 is an enlarged perspective cross-sectional view of the vicinity of the atomizer 210. FIG. 8 is an enlarged cross-sectional view of the vicinity of the atomizer 210. As described above, the atomizer 210 is mainly constituted by a compressed supply (nozzle hole 311 of the case body 300) that allows compressed gas to be ejected substantially in the first direction (z-axis direction), and a liquid supplying member (liquid suction port 213 of the suction route forming body 200) that supplies a liquid toward the ejection route for the compressed gas in accordance with negative pressure that accompanies the ejection of the compressed gas. As shown in FIG. 6, a rectangular nozzle hole 311 is provided on the upper end surface of the compressed gas introduction pipe 301, and as shown in FIG. 7, the nozzle hole 311 is open such that when the nebulizer kit 1 is assembled, the longer side of the nozzle hole 311 is near the liquid suction port 213 and is parallel with the liquid suction port inclined surface 215. The action of the compressed air that is sprayed from the nozzle hole 311 and the liquid supplied from the liquid suction port 213 will be described with reference to FIG. 8. As shown in FIG. 8, a majority of the compressed gas G0 ejected from the nozzle hole 311 is sprayed within a range spanning from the direction of arrow G1 to the direction of arrow G2. Here, as shown in FIG. 6, the nozzle hole 311 is a rectangular opening portion. For this reason, the distribution of the flow amounts of the compressed air ejected in the range spanning from G1 to G2 centered about the +z-axis direction is anisotropic in the xy plane. Specifically, the flow of the compressed air is denser in the yz plane that passes through the nozzle hole 311 and in the region near the nozzle hole 311 and becomes comparatively thinner in the other regions. That is, the long side of the rectangular shape of the nozzle hole 311 is near the liquid suction port 213 and is arranged parallel to the liquid suction port inclined surface 215, thus making it possible to cause the compressed air to act efficiently on the liquid suction port 213. As a result, it is possible to cause the amount of aerosol generated by the atomizer 210 to increase efficiently. Note that the generated aerosol is reflected by the wall surface of the suction route forming body 200 near the liquid suction port 213, and therefore the speed distribution of the jet flow of the aerosol is substantially equal to the first direction (z-axis direction) and regarding the speed components in the direction perpendicular to the first direction, more speed components in the y-axis positive direction are included than speed components in the y-axis negative direction. For this reason, it is possible to efficiently cause the aerosol generated by the atomizer 210 to collide with the inner end wall 123 of the second particle sorting route 121.

Figure 9:
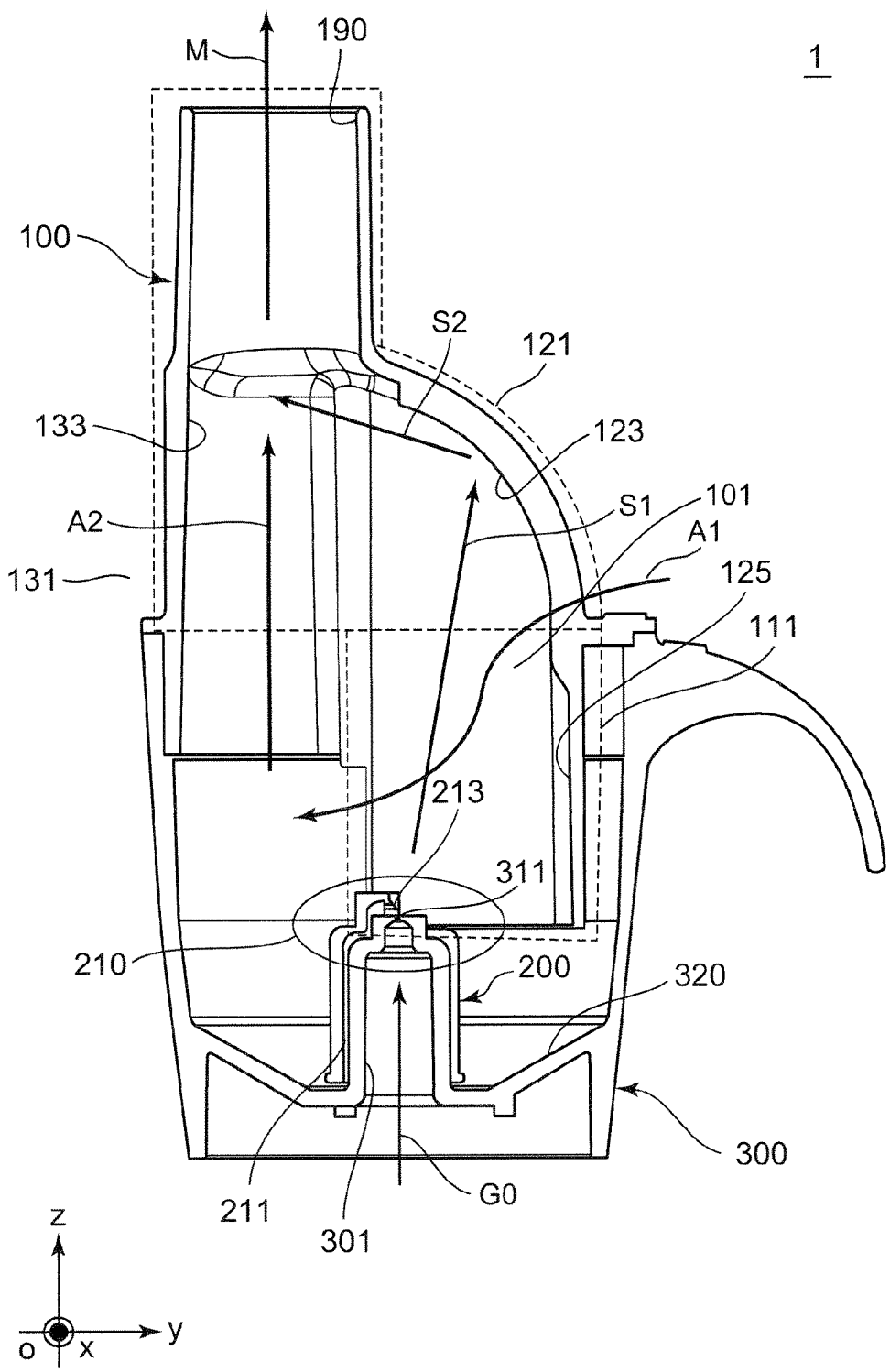
FIG. 9 is a schematic diagram showing a flow of air and a flow of aerosol.
Figure 10:
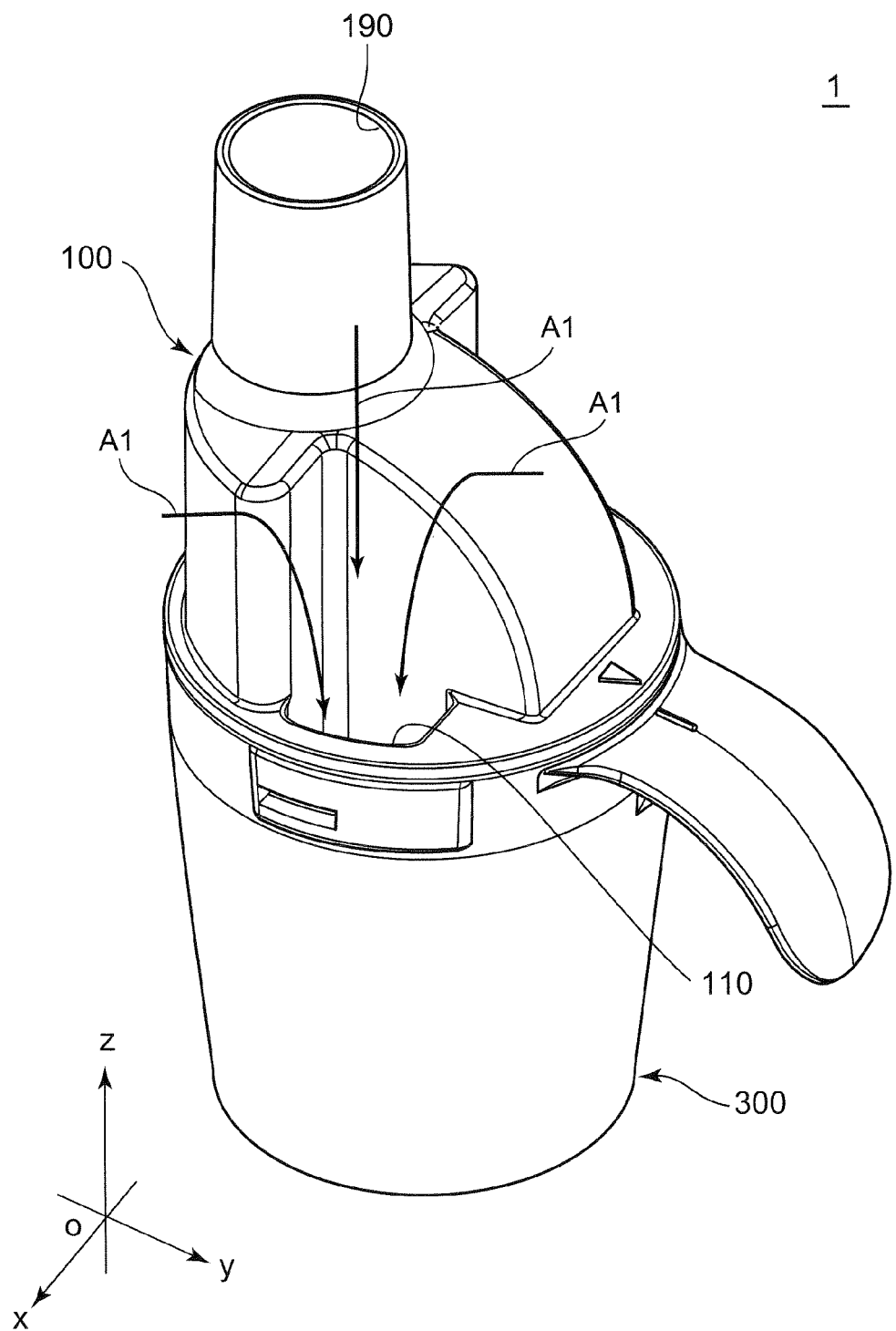
FIG. 10 is a schematic diagram showing a flow of outside air in an outside air introduction hole.
Figure 11:
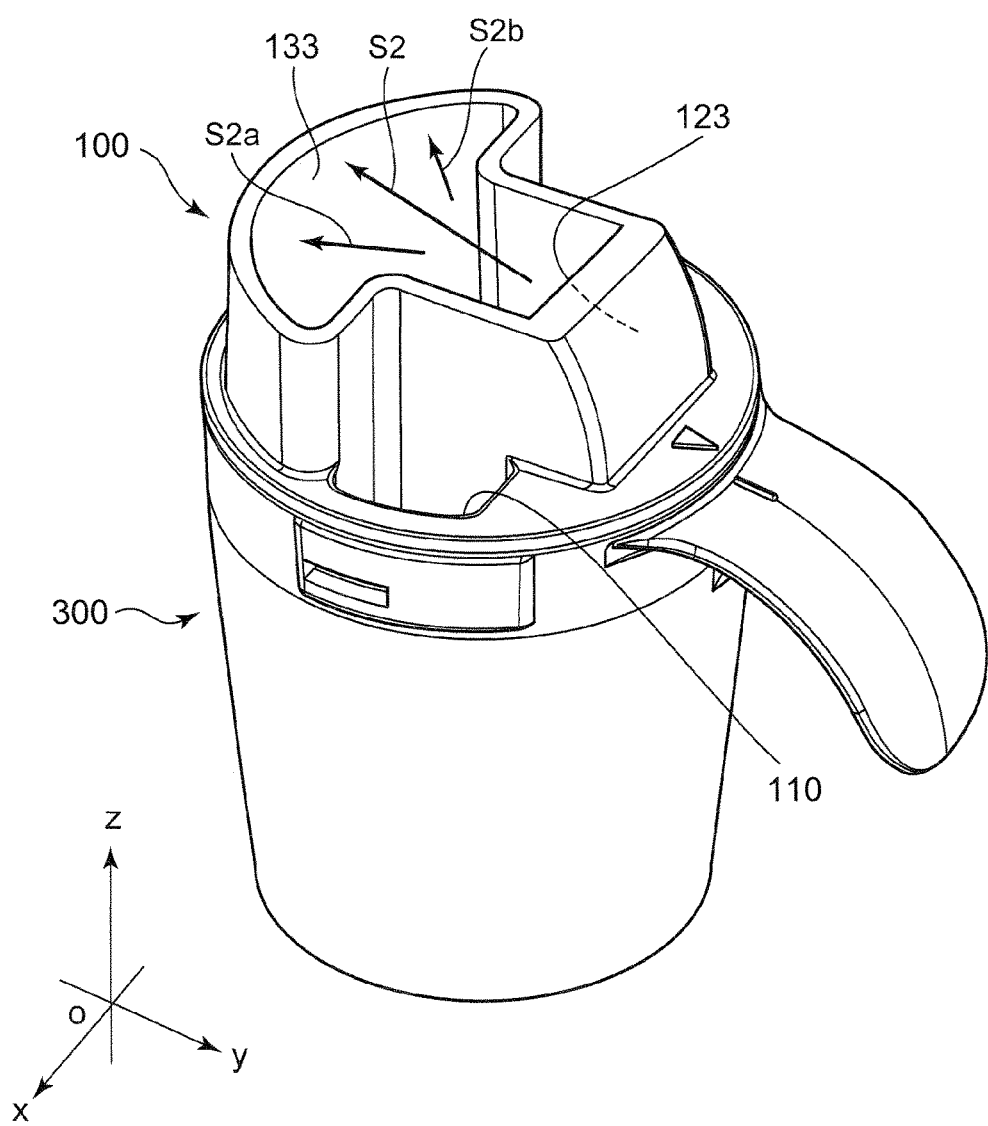
FIG. 11 is a schematic diagram showing a flow of aerosol that flows toward a third particle sorting route from a second particle sorting route.
Figure 12:
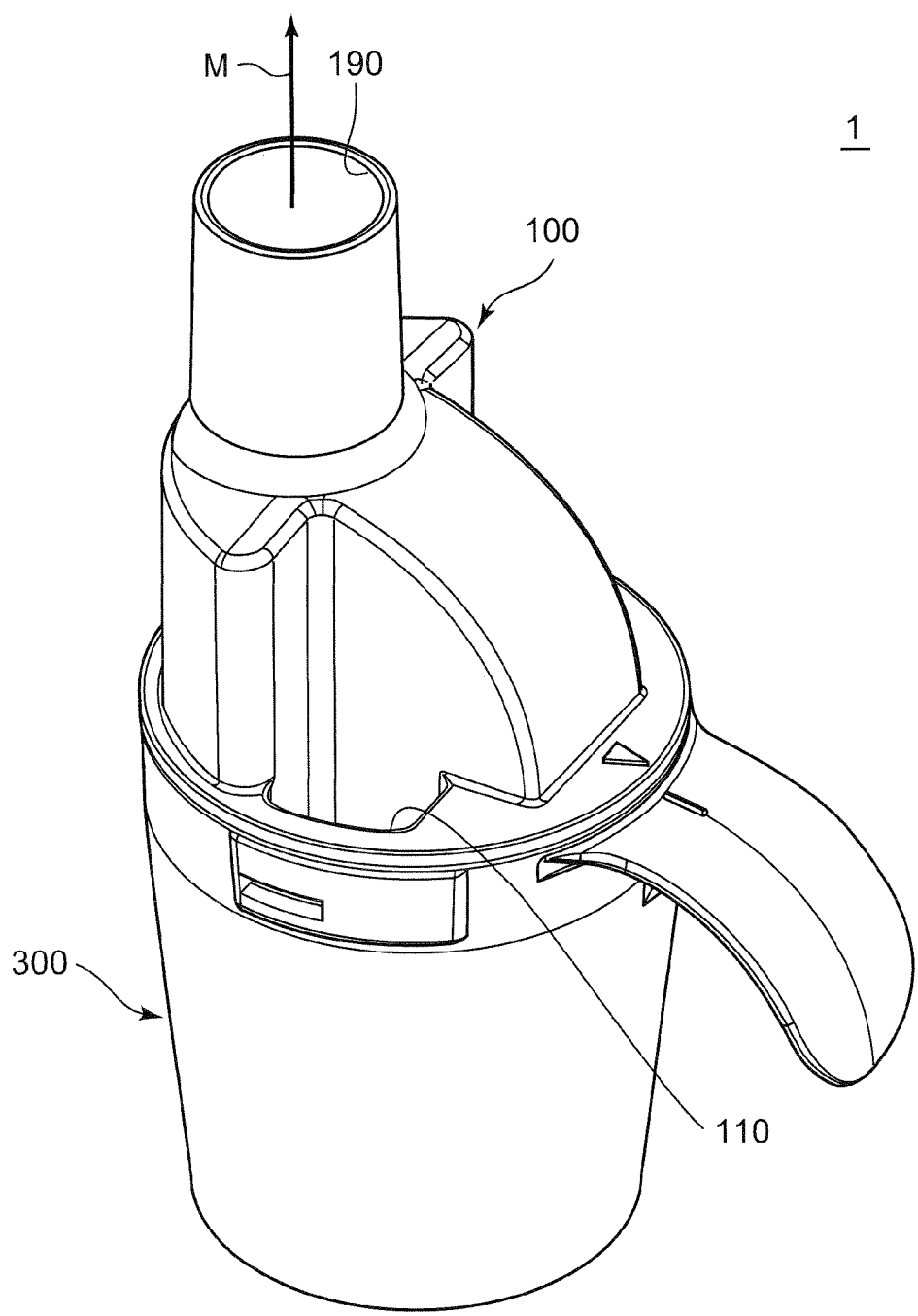
FIG. 12 is a schematic diagram showing a flow of aerosol through a discharge port.

The action of the nebulizer kit 1 will be described with reference to FIGS. 9, 10, 11, and 12. FIG. 9 is a schematic diagram for describing the generation to the discharging of the aerosol. FIG. 10 is a schematic diagram for showing the action of the outer air introduction hole 110. FIG. 11 is a schematic diagram showing a flow of aerosol when the aerosol is guided from the second particle sorting route 121 to the third particle sorting route 131. FIG. 12 is a schematic diagram showing aerosol discharged from the discharge port 190.

With reference to FIG. 9, the compressed gas G0 introduced into the compressed gas introduction pipe 301 is ejected from the nozzle hole 311 centered about the z-axis direction, and flows toward the liquid suction port 213. Negative pressure is generated near the liquid suction port 213 due to the action of the compressed gas that flows near the liquid suction port 213, and due to the action of the negative pressure, the liquid (drug solution, etc.) stored in the liquid storage portion 320 is discharged from the liquid suction port 213 via the suction route forming portion 211.

The liquid discharged from the liquid suction port 213 is disintegrated into fine droplets (particles) due to collision with the compressed gas and the disintegrated particles are mixed with the compressed air to generate an aerosol. The generated aerosol is immediately reflected by the wall surface near the liquid suction port 213 of the suction route forming body 200 and moves toward the direction that is substantially equal to the first direction (z-axis direction) and is slightly inclined in the y-axis positive direction (aerosol S1). The aerosol S1 moves upward through the first particle sorting route 111, collides with the inner end wall 123 of the second particle sorting route 121, and undergoes particle sorting based on particle diameter due to physical interaction with the inner end wall 123.

At this time, the outer air A1 is introduced through the outer air introduction hole 110 due to the flow of the jet flow of the aerosol moving from the atomizer 210 to the first particle sorting route 111 (FIG. 10). The outer air A1 that was introduced flows through a region separated from the first particle sorting route 111 by the inner partition 101 to reach the lower end of the third particle sorting route 131. After reaching the lower end, the direction of the outer air A1 is changed such that the outer air A1 flows upward through the third particle sorting route 131 (outer air A2).

After undergoing particle sorting by colliding with the inner end wall 123 of the second particle sorting route 121, the direction of the aerosol changes to the second direction (direction that approximately coincides with the y-axis negative direction and is slightly inclined in the +z direction) and the aerosol advances in the third particle sorting route 131 (aerosol S2). In the third particle sorting route 131, the flow path is larger than the flow path of the second particle sorting route 121, and therefore the speed decreases while the aerosol disperses (aerosols S2a and S2b), and a portion of the aerosol reaches the inner wall 133 (FIG. 11). The aerosol that reaches the inner wall 133 is subjected to particle sorting that is similar to the particle sorting performed due to the physical interaction with the inner end wall 123 on the second particle sorting route 121. The aerosol subjected to particle sorting is transported to the discharge port 190 on a flow of outside air traveling upward from the lower portion of the third particle sorting route 131 and is discharged (FIG. 12).

Figure 13:
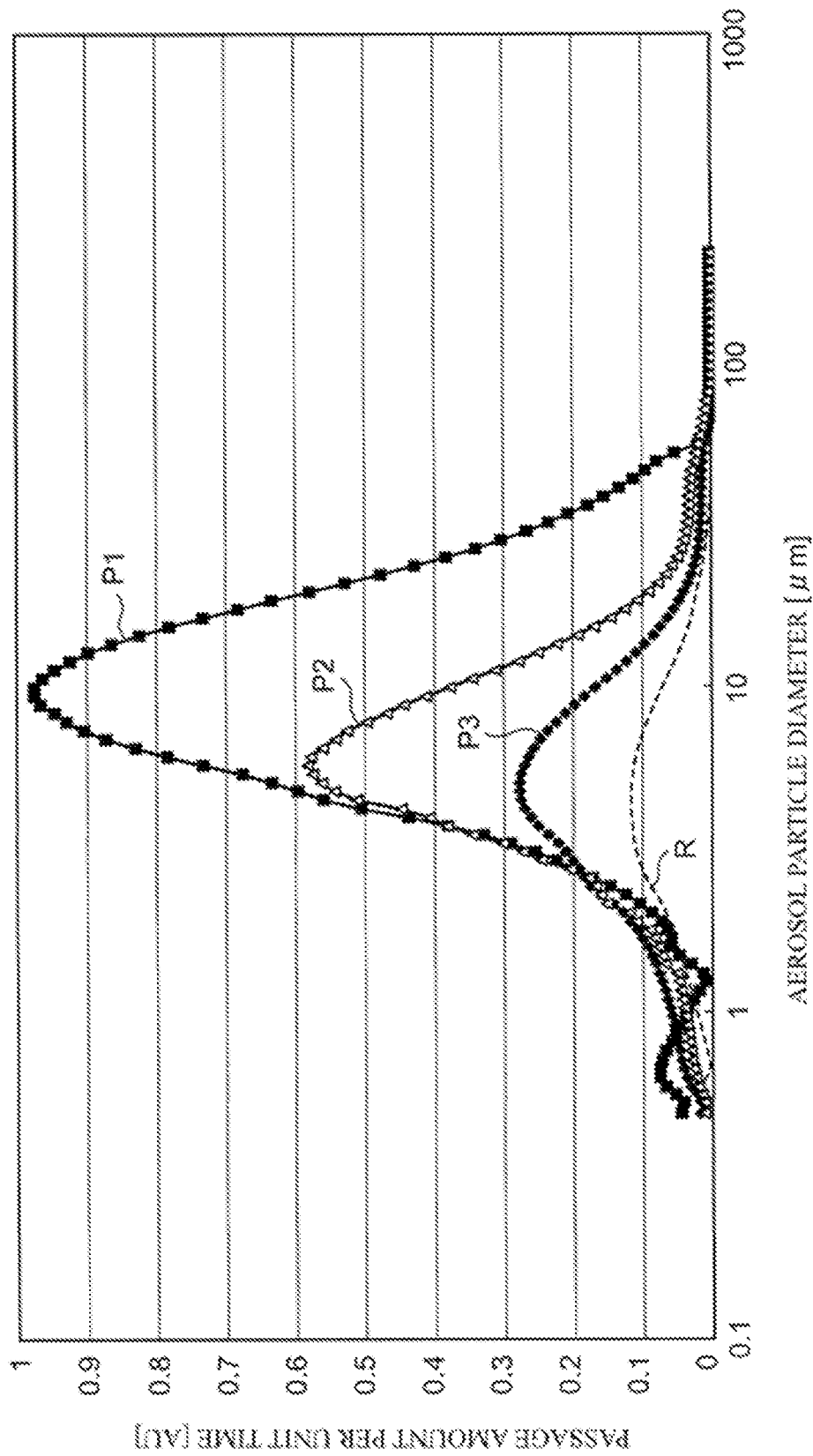
FIG. 13 is a graph showing an effect of particle sorting in a particle sorting route.
Figure 14:
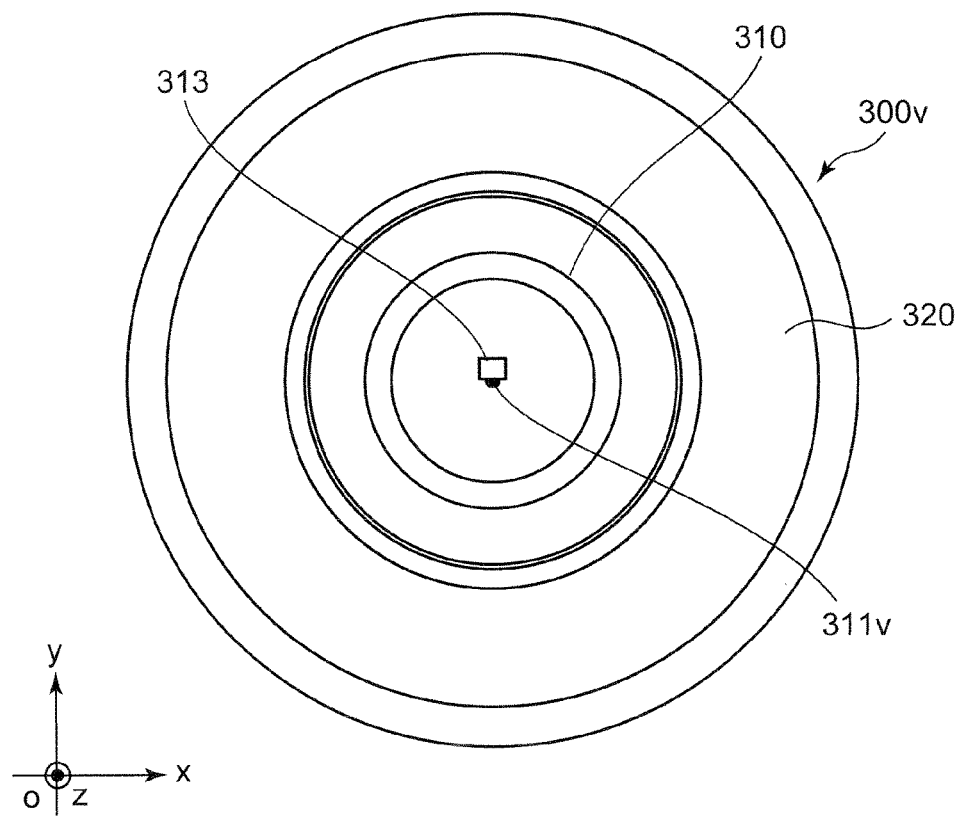
FIG. 14 is a plan view of the case body according to a modified example of a preferred embodiment of the present invention.
Figure 15:
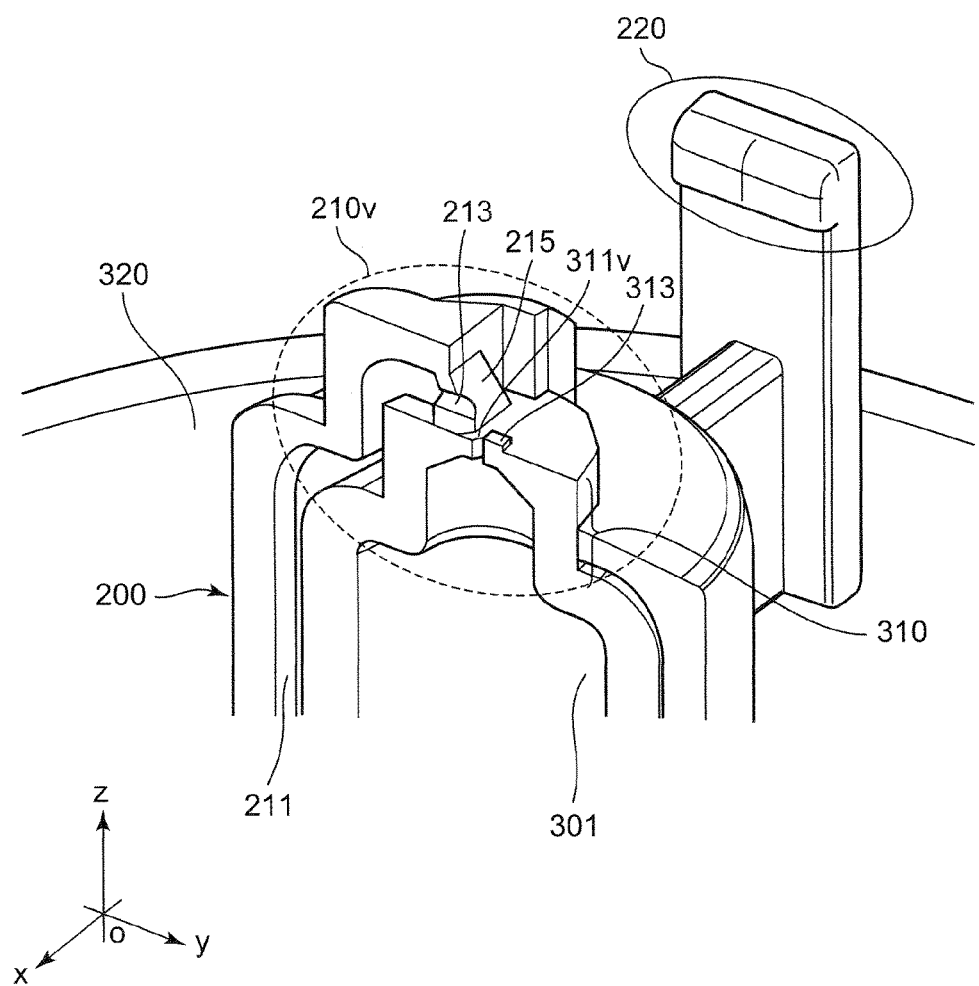
FIG. 15 is an enlarged cross-sectional perspective view showing a configuration of an atomizer according to the modified example.
Figure 16:
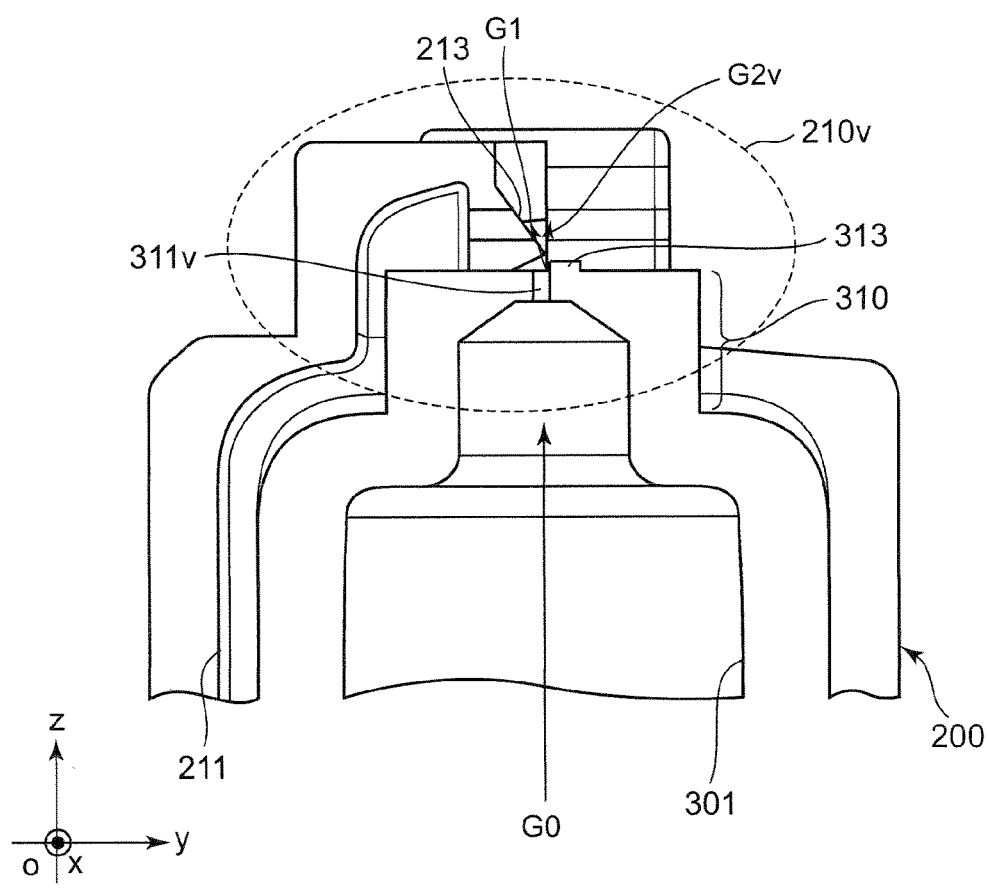
FIG. 16 is an enlarged cross-sectional view showing a configuration of an atomizer according to the modified example.

FIG. 13 is a graph showing a particle diameter distribution of liquid particles included in the aerosol generated by the atomizer 210 of the nebulizer kit 1. The vertical axis of the graph indicates the droplet flow amount per unit time (mass/time), and the horizontal axis indicates the particle diameter of the droplets (microns). Plot P1 is the droplet flow amount per unit time measured in the atomizer 210 under predetermined conditions, plot P3 is the droplet flow amount per unit time measured in the discharge port 190 under the same conditions, and plot P2 is the estimated droplet flow amount per unit time in the portion connecting the second particle sorting route 121 and the third particle sorting route 131, which is measured using the two measurement results (plot P1 and plot P2). Also, plot R is the droplet flow amount per unit time at an aerosol discharge port 1170 (FIG. 18) of a conventional nebulizer kit 1000, which is measured under almost the same conditions.

Upon comparing plot 3 and plot R, it is understood that plot P3 contains more droplets with a relatively small particle diameter than plot R. This means that at the discharge port 190, droplets with relatively small particle diameters are often held in the aerosol in the nebulizer kit 1 according to the present preferred embodiment. Also, the area of the region surrounded by the plot P3 and the plot R on the horizontal axis signifies the total amount of droplets discharged in a unit time from the discharge port 190 (or from the aerosol discharge port 1170), and the graph shows that the nebulizer kit 1 according to the present preferred embodiment can discharge more droplets than the conventional nebulizer kit 1000. Thus, with the nebulizer kit 1 according to the present preferred embodiment, the efficiency of using the compressed gas supplied from the compressor is improved in comparison with the conventional nebulizer kit 1000.

A nebulizer kit according to a modified example of the above-described preferred embodiment will be described next. The present modified example differs from the nebulizer kit of the above-described preferred embodiment in that the configuration of the case body is different. The present modified example may have the same configuration as the nebulizer kit 1 of the above-described preferred embodiment, except for the configuration of the case body. In the present modified example as well, the case body and the suction route forming body form an atomizer 210*v* that generates aerosol by atomizing a liquid, similarly to the above-described preferred embodiment. Hereinafter, the configuration of the case body 300*v* according to the present modified example and the atomizer 210*v* formed using the case body 300*v* and the suction route forming body 200 will be described. Note that description of portions in the configuration of the present modified example that may have a configuration similar to that of the above-described preferred embodiment will be omitted as appropriate.

FIG. 14 is a plan view showing a configuration of the case body 300*v*. As shown in FIG. 14, a D-shaped nozzle hole 311*v* is provided on the upper end surface of the compressed gas introduction pipe 301 and a directing elongated portion 313 for defining the ejection direction of the compressed air is further provided at portion in the periphery of the nozzle hole 311*v*. The particle sorter 100 (FIG. 1, etc.) can be fit by being aligned such that when fit on the case body 300*v*, the directing elongated portion 313 is located on the same side as the first particle sorting route 111 and the like with respect to the nozzle hole 311*v* (located directly under the first particle sorting route 111 and the like).

Next, details of the configuration of the atomizer 210*v*, which is formed using the case body 300*v*, will be described. FIG. is an enlarged perspective cross-sectional view near the atomizer 210*v*. FIG. 16 is an enlarged cross-sectional view near the atomizer 210*v*. Similarly to the atomizer 210 according to the above-described preferred embodiment, the atomizer 210*v* is mainly constituted by a compressed supply (D-shaped nozzle hole 311*v* of the case body 300*v*) that allows the compressed gas to be ejected substantially in the first direction (z-axis direction), and a liquid supplying member (liquid suction port 213 of the suction route forming body 200) that supplies the liquid to the ejection route for the compressed gas in accordance with the negative pressure accompanying the ejection of the compressed gas.

As shown in FIGS. 15 and 16, the directing elongated portion 313 is formed by extending a portion of the wall surface of the compressed supply (nozzle hole 311v) located on the side of the nozzle hole 311v opposite to the liquid suction port 213 substantially in the first direction (z-axis direction). The directing elongated portion 313 restricts the ejection direction for the compressed gas G0 ejected from the nozzle hole 311v and acts such that a majority of the compressed gas is ejected in a direction range spanning from arrow G1 to arrow G2v (FIG. 16). Accordingly, in the atomizer 210v, a majority of the compressed air flows toward the liquid suction port 213, and thus the efficiency of generating the negative pressure near the liquid suction port 213 improves, the efficiency of sucking up the liquid sucked up along the suction route forming portion 211 is improved, and the efficiency of generating the aerosol is improved. Note that the generated aerosol is reflected by the wall surface of the suction route forming body 200 near the liquid suction port 213, and therefore the distribution of the speed of the jet flow of the aerosol is substantially equal to the first direction (z-axis direction), and regarding the speed components in the direction perpendicular to the first direction, more speed components in the y-axis positive direction are included than speed components in the y-axis negative direction. For this reason, it is possible to cause the aerosol generated by the atomizer 210v to efficiently collide with the inner end wall 123 of the second particle sorting route 121.

Thus, with the atomizer 210v, the nozzle hole 311v ejects the compressed gas G0 approximately centered about the z-axis direction, and a majority of the compressed gas G0 flows in a direction toward the liquid suction port 213 due to the action of the directing elongated portion 313. For this reason, in the present modified example, the efficiency of generating the aerosol is further improved, and as a result, the amount of aerosol discharged from the discharge port 190 (FIG. 1, etc.) is increased.

In other words, under the same predetermined conditions, in the case of comparing the atomizer 210v of the present modified example and a comparative atomizer having the same configuration as the atomizer 210v except that there is no directing elongated portion 313, the aerosol generation amount per unit time of the atomizer 210v of the present modified example exceeds the aerosol generation amount per unit time of the comparative atomizer. To give a description using the plots in FIG. 13 as an example, it is understood that the configuration of the atomizer 210v has an effect of further increasing the area (amount of aerosol ejected by the atomizer per unit time) of the region surrounded by the plot P1 and the x axis (horizontal axis). That is to say, enlargement of the area of the region surrounded by the plot P1 and the x axis (horizontal axis) signifies an increase in the area (aerosol passage amount per unit time of the discharge port 190) of the region surrounded by the plot P3 and the x axis (horizontal axis). Thus, the atomizer 210v contributes to the improvement of the aerosol ejection performance of the nebulizer kit.

Note that in the present modified example, the nozzle hole 311v was a D-shaped opening portion, but a rectangular opening portion may be used similarly to the above-described preferred embodiment.

Note that it need not be mentioned that the opening area of the nozzle holes 311 and 311v, or in other words, the representative dimension of the D shape and the dimensions of the long and short sides of the rectangular shape need only be set as appropriate with consideration given to the capability of the compressor in the main body (not shown).

Note that a geometric shape having a curvilinear outline, such as a circle or an ellipse, or a polygonal shape such as a square or a triangle may be used instead of a D shape and a rectangular shape as the opening shape of the nozzle holes 311 and 311v.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A nebulizer kit comprising:
an atomizer that generates an aerosol by atomizing a liquid and ejects the aerosol in a first direction; and
a particle sorting route that is in communication with the atomizer, and sorts particles of the liquid included in the aerosol so as to adjust a particle diameter distribution of the particles of the aerosol, and thereafter guides the aerosol to a discharge port; wherein
the particle sorting route includes a first particle sorting route that extends in the first direction from the atomizer and has a uniform or substantially uniform cross-sectional area in the first direction, a second particle sorting route that is in communication with the first particle sorting route and includes an inner end wall that directly faces the atomizer and has a curvature that curves from the first direction toward a second direction, and a third particle sorting route that is in communication with the second particle sorting route and extends in a direction parallel or substantially parallel to the first direction in a state of being shifted in a direction perpendicular or substantially perpendicular to the first direction;
the first particle sorting route guides the aerosol ejected from the atomizer in a direction equal or substantially equal to the first direction to the second particle sorting route in the first direction;
the inner end wall of the second particle sorting route guides the aerosol in the second direction, which is inclined with respect to the first direction, such that particles, among the particles of the aerosol, that have a particle diameter of a certain value or more collide with and attach to the inner end wall; and
the third particle sorting route has a cross-sectional area greater than an entire cross-sectional area of the second particle sorting route in the first direction, and allows the aerosol to flow to the discharge port, particles with the particle diameter of the certain value or more among the particles being attached to an inner wall thereof that is parallel or substantially parallel with the first direction and is inclined with respect to the second direction.

2. The nebulizer kit according to claim 1, wherein
the second particle sorting route and the third particle sorting route overlap with respect to the first direction; and
in the third particle sorting route, outer air is allowed to flow toward the discharge port from a side near the atomizer with respect to a region at which the third particle sorting route overlaps with the second particle sorting route with respect to the first direction.

3. The nebulizer kit according to claim 1, wherein
the third particle sorting route extends in a direction parallel or substantially parallel to the first direction over a certain length or more from a terminal end of the inner end wall of the second particle sorting route on a side opposite to the first particle sorting route.

4. The nebulizer kit according to claim 1, wherein the atomizer includes:
- a compressed gas supply that ejects compressed gas in a direction parallel or substantially parallel to the first direction; and
- a liquid supplying member that is arranged on one side in an orientation of intersecting the first direction in a periphery of an opening portion of the compressed gas supply, and supplies a liquid to an ejection route for the compressed gas in accordance with negative pressure accompanying ejection of the compressed gas; and
- the compressed gas supply is such that on another side, which is opposite to the one side in the periphery of the opening portion, a wall surface of a compressed gas supply route is extended in or substantially in the first direction past an outer surface on the one side of the compressed gas supply.

5. The nebulizer kit according to claim 1, wherein the atomizer ejects the aerosol such that in a speed distribution of a jet flow of the aerosol with respect to a direction perpendicular or substantially perpendicular to the first direction, more speed components in a direction opposite to the second direction are included than speed components in the second direction.

6. A nebulizer comprising:
- a main body including a compressor that discharges compressed gas;
- a compressed gas pipe through which the compressed gas discharged from the compressor is introduced; and
- the nebulizer kit according to claim 1 that generates the aerosol using the compressed gas supplied through the compressed gas pipe.

* * * * *